US00PP12188P2

(12) United States Plant Patent
Kester et al.

(10) Patent No.: US PP12,188 P2
(45) Date of Patent: Nov. 6, 2001

(54) PRUNUS ROOTSTOCK NAMED 'NICKELS'

(75) Inventors: Dale E. Kester, Davis, CA (US); Richard N. Asay, Thayne, WY (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/404,207

(22) Filed: Sep. 23, 1999

(51) Int. Cl.[7] ..... A01H 5/00

(52) U.S. Cl. ..... Plt./156

(58) Field of Search ..... Plt./156

*Primary Examiner*—Bruce R. Campell
*Assistant Examiner*—A Para

(57) ABSTRACT

An improved almond×peach clonal rootstock is provided that was the product of a planned breeding program. It can be used to particular advantage when growing almond cultivars for commercial fruit production. The new rootstock provides excellent anchorage through the presence of a well-branched network of deep roots. The growth habit is vigorous and uniform. Efficient asexual propagation by the use of hardwood cuttings is possible. The resulting plants are well amenable to transplantation and storage and exhibit good pest resistance and winter hardiness. A wide adaptation to nursery growing conditions is achieved. Additionally, the long tern survival of the rootstock has been found to be superior to that of 'Hansen 536' (U.S. Plant Pat. No. 5,173) and 'Hansen 2168' (U.S. Plant Pat. No. 5,210).

4 Drawing Sheets

SUMMARY OF THE INVENTION

Figure 1:
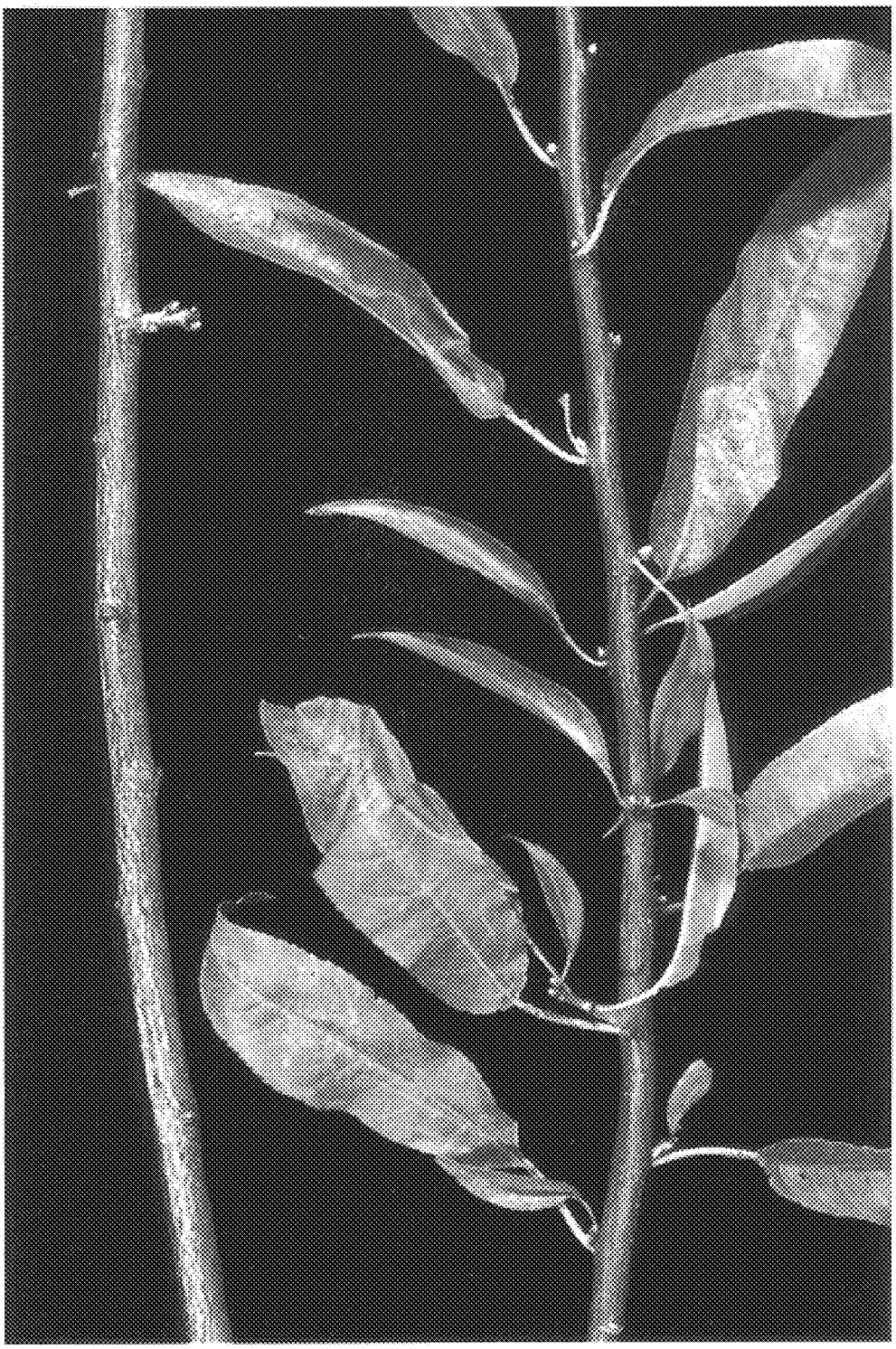

The new variety of the present invention originated during the summer of 1973 and was a product of planned almond× peach hybrid rootstock breeding program carried out at the research and experimental plant nursery and orchards of the Department of Pomology at the University of California, Davis, Yolo Country, Calif. Other almond×peach rootstock varieties that resulted from the work of another associated with the same breeding program include 'Hansen 2168' (U.S. Plant Pat. No. 5,210), and 'Hansen 536' (U.S. Plant Pat. No. 5,173).

The female parent (i.e., seed parent) of the new variety of the present invention was the almond variety 'Sel. 5-33' (non-patented in the United States) that had been produced by the crossing of the 'McLish' variety (non-patented in the United States) and the 'Reams' variety (non-patented in the United States). The male parent (i.e., pollen parent) of the new variety of the present invention was the peach 'Nemaguard' variety (non-patented in the United States) which is a commercially important rootstock used in California. Such pollen parent is believed to be a hybrid of peach and *Prunus mira*. The parentage of the new variety can be summarized as follows:

Almond 'Sel. 5-33'×Peach 'Nemaguard'.

The cross that resulted in the creation of the new variety was carried out by hand and the resulting progeny were carefully observed and studied. It was found that a single plant of the new variety of the present invention resulted from such controlled plant breeding and such plant has been carefully preserved in view of its highly desirable combination of characteristics. Had this new plant not been discovered and preserved it would have been lost to mankind.

It was found that the new almond×peach clonal rootstock of the present invention possesses the following combination of characteristics:

(a) Forms young branches having a strong reddish-brown overcolor,
(b) Forms well-branched deep roots that provide excellent anchorage,
(c) Readily undergoes propagation by the use of hardwood cuttings,
(d) Exhibits a vigorous and uniform growth habit,
(e) Is well amenable to transplantation and practices commonly used in commerical almond production,
(f) Forms a fruit and stone having a sharp protruding tip,
(g) Is resistant to root-knot nematodes *Meloidegyne incognita acrita* and *Meloidegyne javanica*, and
(h) Is more cold hardy than 'Hansen 2168' (U.S. Plant Pat. No. 5,210) and 'Hansen 536' (U.S. Plant Pat. No. 5,173).

The new variety of the present invention exhibits a vigor that is comparable to 'Hansen 2168' 'and Hansen 536'. Such vigor is greater than that of other peach rootstocks, almond, and 'Marianna 2624'. Resistance to nematodes is substantially the same as that of the parent 'Nemaguard' variety which is widely used successfully throughout California for both almond and peach cultivars in nematode affected sites. The new variety readily roots by the use of dormant hardwood cuttings. The ability to undergo propagation by hardwood cuttings is comparable to that of 'Hansen 536'. The new variety has demonstrated an ability to better resist transplanting failures and storage problems that are sometimes observed with 'Hansen 536', and adapts well to practices commonly used in commercial almond production. Also, long term rootstock field tests have shown a greater survival ability than other rootstocks including 'Hansen 536' and 'Hansen 2168'. The new variety exhibits a higher chilling requirement than 'Hansen 536' and 'Hansen 2168' which makes possible its utilization under a wider range of soil and climate conditions. The flowers are very large and conspicuous and are reddish pink in coloration.

Beginning in 1973 the new variety of the present invention has been reproduced at Davis, Calif. by the use of hardwood cuttings. The new variety also has been reproduced by budding. Such propagation has confirmed that the characteristics of the new cultivar are stable and are reliably transmitted to subsequent generations.

The new variety is particularly well suited for use as an improved rootstock for the growing of almond cultivars. It additionally is believed to be suitable for the growing of peach, plum, and prune cultivars.

It should be understood that the inherently exhibited characteristics of the new variety described herein may vary somewhat when grown under differing climatic and growing conditions.

The new variety of the present invention was assigned Testing No. PA1-82. It subsequently has been named the 'Nickels' variety following testing at the Nickels Estate Research Farm at Colusa County, Calif.

BRIEF DESCRIPTION OF THE PHOTOGRAPHS

The accompanying photographs show typical specimens of plant material of the new variety as depicted in color as nearly true as is possible to make the same in color illustrations of this character. The depicted plants of the new variety were grown Davis, Yolo County, Calif.

FIG. 1 shows one-year-old shoots during early August. On the right is a foliage-bearing shoot wherein the reddish-brown colored epidermis, and bud arrangement at individual nodes are depicted. Pointed shoot buds and larger round flower buds are visible. On the left is shown a somewhat older portion of a one-year-old shoot wherein vertical striations of the outer surface are visible which were caused by the stretching of the bark during growth. A short annual spur produced at a node also is shown.

Figure 2:
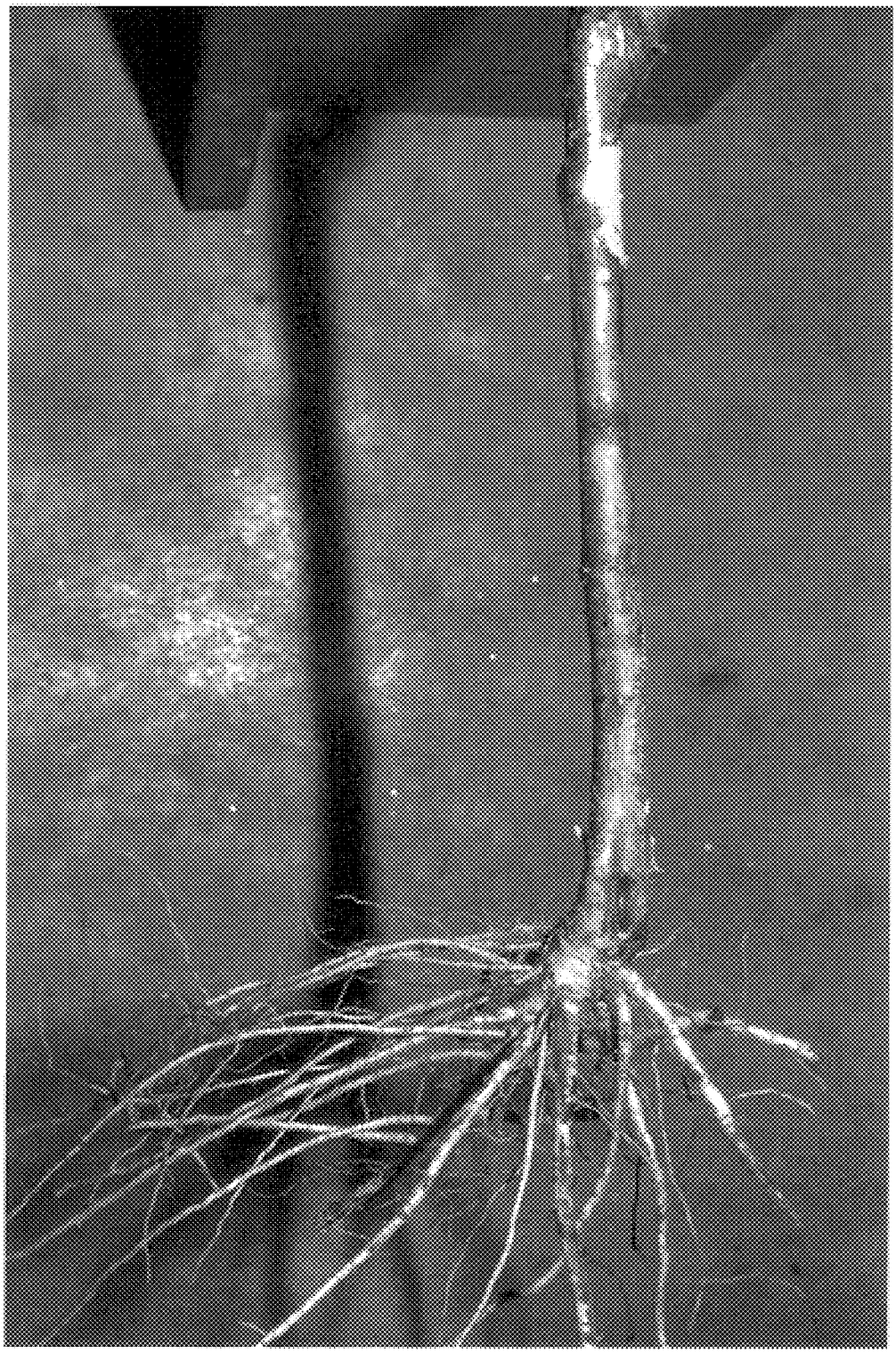

FIG. 2 shows the typical root configuration of a rooted cutting of the new variety which was dug and observed one year after is was placed in the nursery row. Such root system is extensive and deep. The roots are straight, somewhat tapering and radiate outwardly and downwardly from the cutting from which they originate. The base of a budded shoot is shown at the very top of the photograph. The advantageous placement and spreading character of the roots are apparent.

Figure 3:
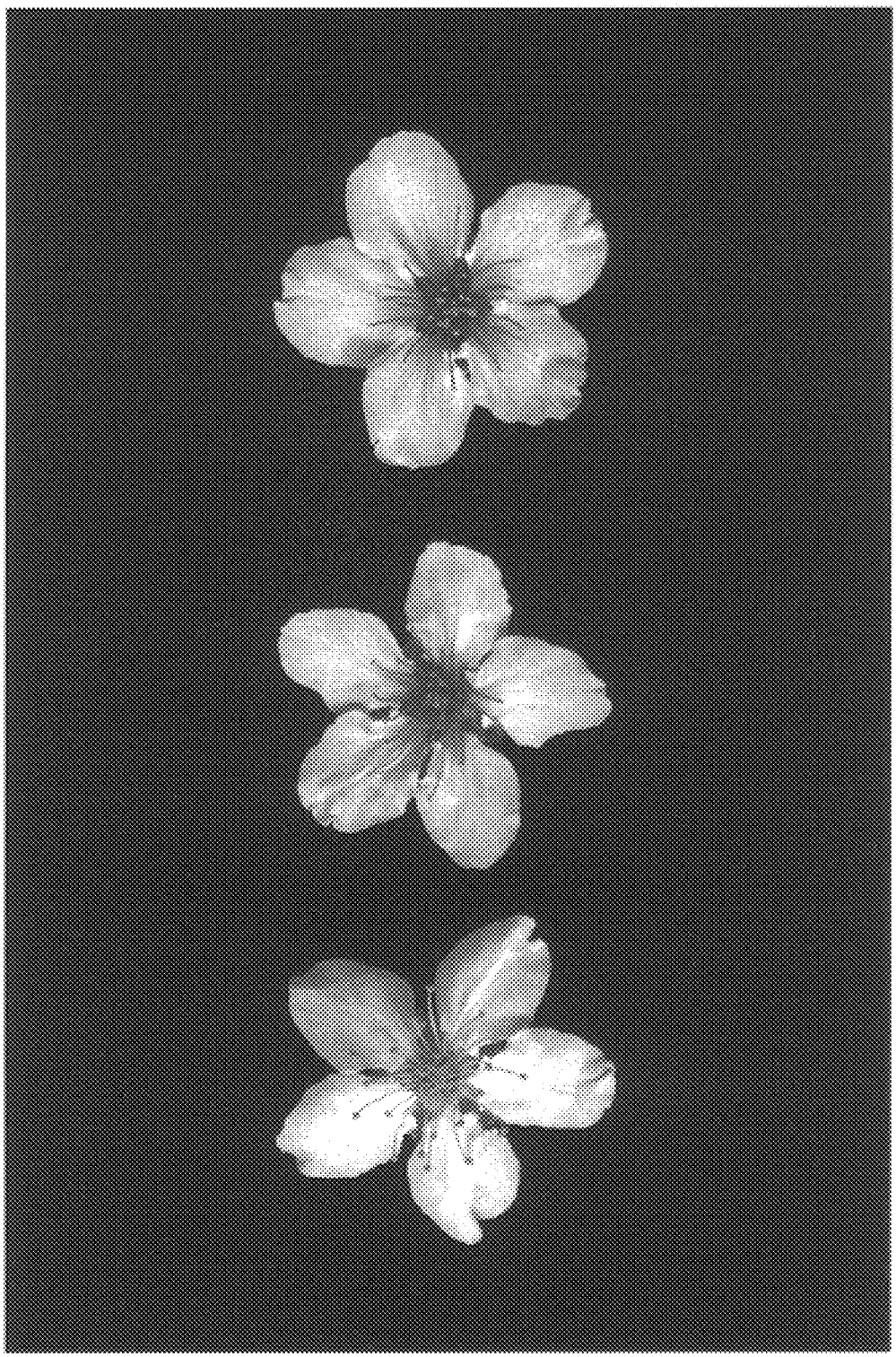

FIG. 3 shows three typical flowers in various states of maturity with the youngest flower being at the top and the oldest flower being at the bottom. It will be noted that more pink is present in the youngest flower and that there is a gradual fading of the pink coloration with age.

Figure 4:
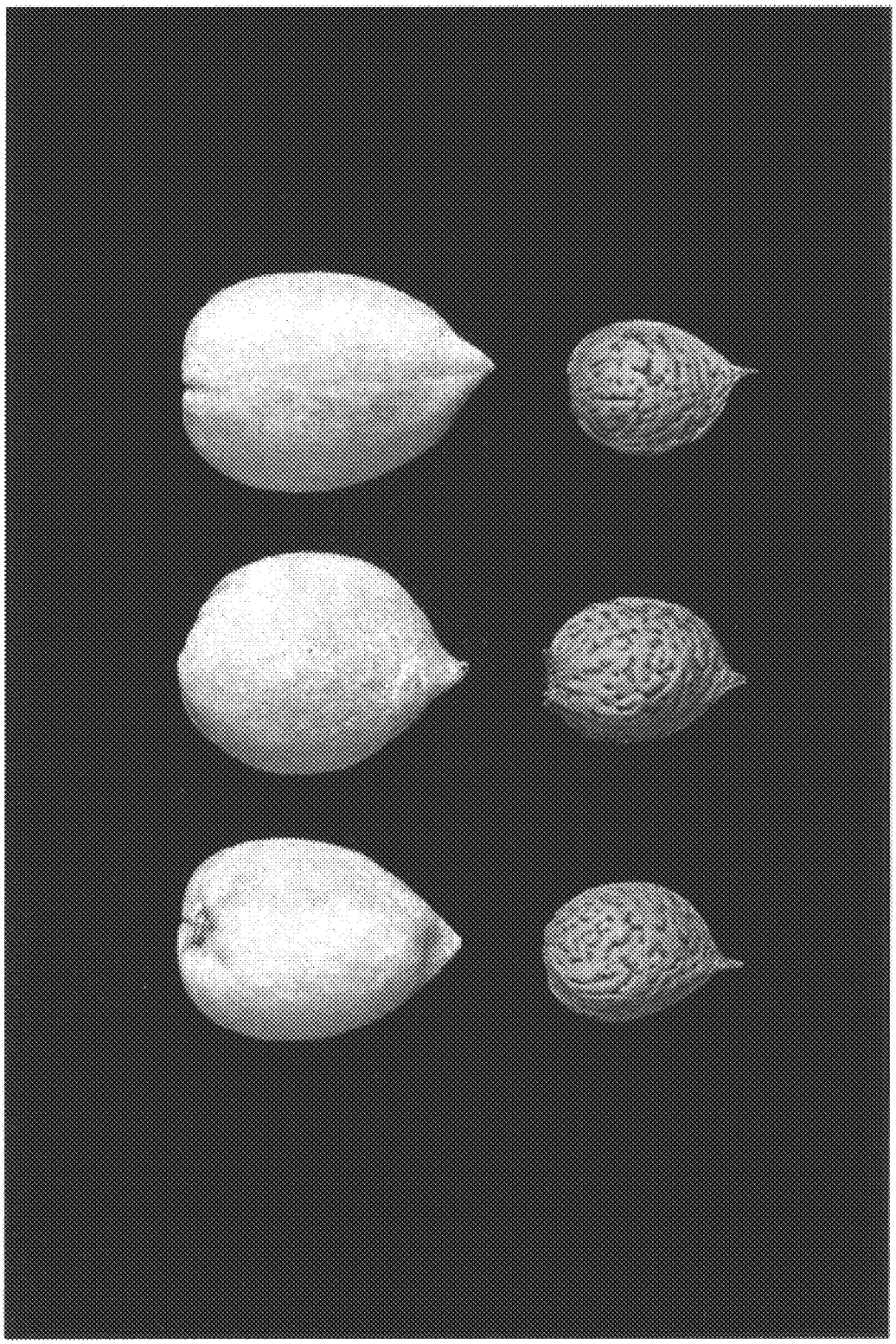

FIG. 4 shows different views of typical specimens of the immature fruit (left) and round-oval pit (right) of the new variety. When viewing the immature fruit on the left, at the top is shown the ventral or end portion, at the middle is shown a side view, and at the bottom is shown a dorsal or front view. The prominent elongated apical tip or beak of the immature fruit is depicted. When viewing the pits on the right, characteristic surface depressions (i.e., shallow grooves and round depressions) as well as the sharp apical tip of the pits are apparent.

DETAILED DESCRIPTION

The following is a detailed description of the new 'Nickels' variety while grown at Davis, Yolo County, Calif. The color chart used in the designation of color expressed hereafter is that of Maerz and Paul, First Edition (1930). Other color designations are to be accorded their usual dictionary significance.

Botanical classification: Almond×Peach hybrid, cv. 'Nickels'.

Tree:

*Size.*—Large. Commonly reaches a mature height of approximately 13 to 14 feet on average.

*Vigor.*—Vigorous, with vegetative shoots commonly extending 3 to 5 feet in length on a young plant.

*Form.*—Medium upright, vase-shaped, uniform, and spreading due to long shoots, intermediate almond and peach, but tending to be more towards peach. The branch angles are approximately 30 to 60 degrees depending upon the location of the branch and degree of pruning.

Roots:

*Description.*—Well-branched, numerous, prominent, vigorous, relatively thick, relatively straight, somewhat tapering, and radiate outwardly and downwardly from the cutting from which they originate (See FIG. 2). Good anchorage is made possible.

Trunk:

*Diameter.*—Medium. The average trunk diameter of six year-old trees measured 12 inches above the ground is approximately 6.2 inches.

*Texture.*—Possesses vertical fissures and striations.

*Color.*—Gray-brown with the older bark being more brown with a whitish overcolor. The coloration is generally (P15 H6).

Branches:

*Shoots.*—Long and vigorous with numerous lateral current-season shoots.

*Color.*—Green undercolor with a reddish-brown overcolor with vertical striations upon exposure to the sun. The second season growth is very reddish-brown. The outer epidermis becomes cracked and striated with growth (See FIG. 1). The coloration of 1 year-old shoots is rustic brown (P7 H11) when exposed, and the undercolor is (P13 L2) when unexposed. The coloration of older shoots is auburn (P7 C11).

*Lenticels.*—Prominent and moderate in number. The size commonly ranges from approximately 5 to 8 mm×2 mm depending upon location. The coloration is macaroon (P12 H7).

Leaves:

*Size.*—Large and borne on vigorous shoots, lanceolate and wavy. New leaves are grass green (P1 21 L5) on the upper surface and cress (P1 22 K6) on the under surface. Mature leaves are art green (P1 22 L7) on the upper surface and peridot (P1 22 L6) on the under surface. Vigorous leaves commonly measure approximately 44.6 cm in length and 14.9 cm in width. The petioles commonly measure approximately 2.1 cm in lenfth.

*Thickness.*—Relatively thin.

*Texture.*—Relatively smooth.

*Color.*—Green to olive green (as illustrated).

*Margin.*—Crenate-serrate.

*Petiole.*—Medium length, longer than peach but shorter than almond. Accordingly, the length is intermediate almond and peach.

*Glands.*—Round and commonly number approximately two to four on the petiole near the blade and are non-prominent.

Flowers:

*Bearing.*—Produced primarily laterally on long shoots and are grouped 2 to 3 at a node with a vegetative bud.

*Buds.*—Medium in size, plump, blunt and rounded somewhat pubescent on margins of bud scales, and when mature are green with a reddish overcolor on the exposed parts.

*Blooming time.*—During the first half of March at Davis, Calif., later than approximately 90 percent of the almond varieties and generally concurrent with many peach varieties.

*Size.*—Single, possess 5 petals, very large showy, approximately 1¾ inch in diameter when fully open, and conspicuous with overlapping petals (See FIG. 3). The petals are slightly larger than wide. They commonly are approximately 10 to 11/16 inch in length and approximately 9 to 10/16 inch in width.

*Color.*—Pink with a reddish blotch at the base when opening. Gradually fades to light pink and subsequently to almost white as the blossoms mature. The exposed bud tip is (P1 E4) in coloration. The petal coloration is generally (P1 C7) and (P4 G6) at the base.

*Peduncle.*—Glabrous, smooth and green in coloration.

*Calyx.*—Green when first emerges and quickly develops reddish streaks which expand to reddish-brown over the entire surface.

*Sepals.*—Green covered with red as the flower opens, 5 in number and regularly arranged around the calyx. The sepal coloration is garnet (P7 J6).

*Petals.*—Round to oval, somewhat undulating with a notch at the apex (See FIG. 3).

*Stamens.*—The rose-colored filaments are long and straight and fade to white on the upper one-half with maturity. The stamens are upright, approximately ¼ to ½ inch in length, and (P4 L3) in coloration.

*Anthers.*—Yellow (P12 K9) in coloration.

*Filaments.*—The coloration is (P4 L3).

*Pollen.*—The coloration is lime (P11 L5).

*Pistils.*—Whitish, tend to be very straight in configuration, the stigma is very pubescent, and commonly extends to just below the height of the stamens. The stigma is narcissus (P10 K4) in coloration.

Fruit:

*Season of maturity.*—Late (September). Dehisces like an almond, but the mesocarp tends not to enlarge. There is some tendency for the mesocarp to stick to the endocarp.

*Bearing.*—Fruit is produced laterally on long shoots like peach and on shorter hanger-type branches having a length of approximately 8 to 12 inches. The overall productivity is medium.

*Form.*—Roundish but commonly uneven between the two sides thereby conveying a lopsided appearance. Such configuration is substantially different than that of 'Hansen 536' and 'Hansen 2168'.

*Flesh.*—Semi-fleshy and whitish in appearance.

*Pubescence.*—Medium in quantity and whitish in appearance.

Stone:

*Form.*—Round-oval with a very long sharp protruding tip and cocoa (P7 E12) in coloration.

*Surface configuration.*—Possesses a network of shallow grooves and round depressions (See FIG. 4). The vertical edge is ridged. The dorsal edge has a depression running the length of the stone.

*Color.*—Light brown and very uniform (as illustrated).

*Kernel.*—Non-edible.

Major use: As a superior rootstock which readily can be reproduced by the use of hardwood cuttings under conventional nursery growing conditions.

Disease resistance: Resistant to Phytophthora root rot during testing to date.

Pest resistance: Good resistance to root-knot nematodes *Meloidegyne incognita acrita* and *Meloidegyne javanica*. Such resistance is believed to be comparable to that of the 'Nemaguard' parent.

Hardiness: Moderately hardy in view of late spring blooming. More cold hardy than the 'Hansen 2168' and 'Hansen 536' varieties. Such hardiness is attributable to a higher chilling requirement than most almond varieties that is similar to that of peach varieties. The plant blooms later and goes dormant in the fall earlier than most almond varieties. For instance, the present variety often goes dormant in the fall two to three weeks earlier than other almond varieties.

Performance: Some tolerance to iron chlorosis is exhibited. Is resistant to blowover due to deep root system. Is more tolerant than 'Hansen 536' to transplanting and handling in the nursery. Orchard testing has shown the new variety generally to be as long lived in the orchard as peach rootstocks and to be more long lived than other almond× peach hybrid clones including 'Hansen 536'.

We claim:

1. A new and distinct variety of almond×peach clonal rootstock tree which exhibits the following combination of characteristics:

(a) Forms young branches having a strong reddish-brown overcolor, (b) Forms well-branched deep roots that provide excellent anchorage, (c) Readily undergoes propagation by the use of hardwood cuttings, (d) Exhibits a vigorous and uniform growth habit, (e) Is well amenable to transplantation and practices commonly used in commercial almond production, (f) Forms a fruit and stone having a sharp protruding tip, (g) Is resistant to root-knot nematodes *Meloidegyne incognita acrita* and *Meloidegne javanica*, and (h) Is more cold hardy than 'Hansen 2168' (U.S. Plant Pat. No. 5,210) and 'Hansen 536' (U.S. Plant Pat. No. 5,173); substantially as illustrated and described.

* * * * *